US009060979B2

(12) United States Patent
Doi

(10) Patent No.: US 9,060,979 B2
(45) Date of Patent: Jun. 23, 2015

(54) ANTIDEPRESSANT

(75) Inventor: Masako Doi, Naruto (JP)

(73) Assignee: OTSUKA PHARMACEUTICAL FACTORY, INC., Naruto-shi, Tokushima (JP)

(*) Notice: Subject to any disclaimer, the term of this patent is extended or adjusted under 35 U.S.C. 154(b) by 1308 days.

(21) Appl. No.: 12/444,144

(22) PCT Filed: Oct. 10, 2007

(86) PCT No.: PCT/JP2007/069721
§ 371 (c)(1),
(2), (4) Date: Sep. 8, 2009

(87) PCT Pub. No.: WO2008/044691
PCT Pub. Date: Apr. 17, 2008

(65) Prior Publication Data

US 2010/0105774 A1 Apr. 29, 2010

(30) Foreign Application Priority Data

Oct. 10, 2006 (JP) ................................ 2006-276611

(51) Int. Cl.
*A61K 31/198* (2006.01)
*A61K 31/7004* (2006.01)

(52) U.S. Cl.
CPC ........... *A61K 31/198* (2013.01); *A61K 31/7004* (2013.01)

(58) Field of Classification Search
CPC ......................... A61K 31/198; A61K 31/7004
USPC ................................................. 514/727, 763
See application file for complete search history.

(56) References Cited

U.S. PATENT DOCUMENTS

| | | | | |
|---|---|---|---|---|
| 2004/0033252 | A1 | 2/2004 | Yamamoto et al. | 424/439 |
| 2004/0071825 | A1* | 4/2004 | Lockwood | 426/72 |
| 2007/0149493 | A1 | 6/2007 | Ross | |
| 2007/0191287 | A1 | 8/2007 | Yamamura et al. | |

FOREIGN PATENT DOCUMENTS

| | | | |
|---|---|---|---|
| JP | 02-172915 | | 7/1990 |
| JP | 03-275631 | | 12/1991 |
| JP | 08-283148 | | 10/1996 |
| JP | 2000-026289 | | 1/2000 |
| JP | 2000-026290 | | 1/2000 |
| JP | 2003-221327 | | 8/2003 |
| JP | 2003-221329 | | 8/2003 |
| JP | 2003-221330 | | 8/2003 |
| JP | 2005-336176 | | 12/2005 |
| RU | 2151596 | C1 | 6/2000 |
| WO | WO 02/34257 | A1 | 5/2002 |
| WO | WO 2005/065692 | A1 | 7/2005 |
| WO | WO 2005/089774 | A1 | 9/2005 |
| WO | WO 2006/077954 | A1 | 7/2006 |

OTHER PUBLICATIONS

Haupt et al. “Abnormalities in glucose regulation associated with mental illness and treatment”. Journal of Psychosomatic Research 52 (2002) 925-933.*

Toshitaka Kido, “Mansei Stress to Hiro” Igaku no Ayumi, vol. 204, No. 5, pp. 365-369, Feb. 1, 2003 (with partial English translation).

English translation of International Preliminary Report on Patentability for corresponding PCT application PCT/JP2007/069721.

Winfried et al., “Psychobiological Aspects of Somatoform Disorders: Contributions of Monoaminergic Transmitter Systems” Neuropsychology, vol. 49, No. 1, pp. 24-29, Jan. 2004.

European search report dated Feb. 12, 2010 for corresponding European application 07829459.2.

Richard J. Wurtman, et al., “Carbohydrates and Depression,” Scientific American, Jan. 1989, pp. 68-75.

* cited by examiner

*Primary Examiner* — Renee Claytor
(74) *Attorney, Agent, or Firm* — Hogan Lovells US LLP

(57) ABSTRACT

An antidepressant containing, as an active ingredient, at least one compound selected from a branched amino acid, a pharmaceutically acceptable salt thereof and a derivative thereof.

16 Claims, 1 Drawing Sheet

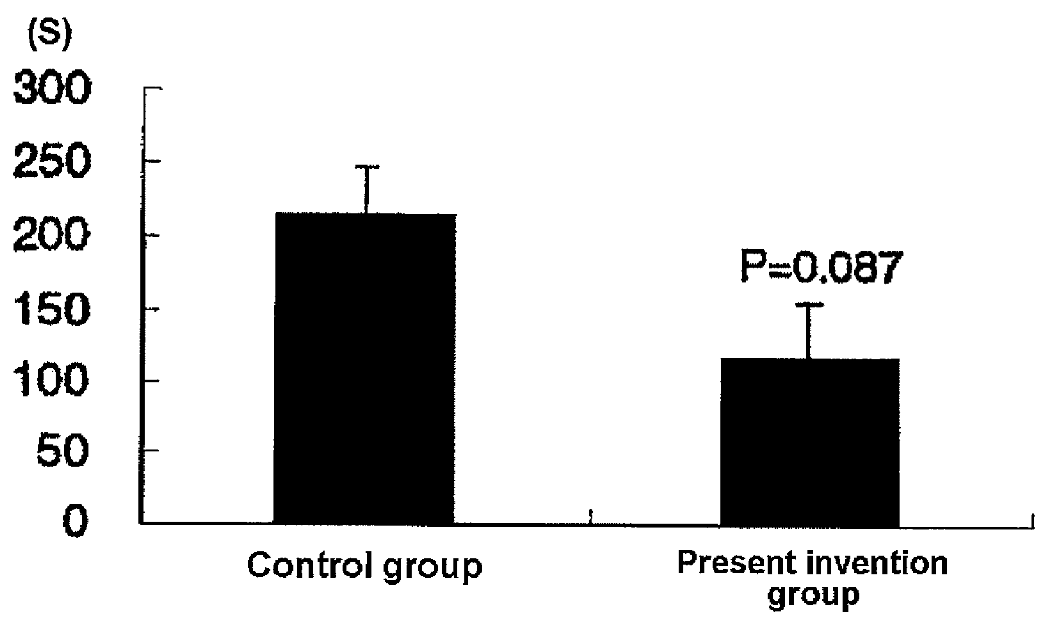
(S)
300
250
200
150
100
50
0
P=0.087
Control group
Present invention group

ANTIDEPRESSANT

CROSS-REFERENCE TO THE RELATED APPLICATIONS

The present application is a national stage of international application No. PCT/JP2007/069721, filed on Oct. 10, 2007, which also claims the benefit of priority under 35 USC 119 of Japanese Patent Application No. 2006-276611, filed on Oct. 10, 2006, the entire contents of which are incorporated herein by reference.

TECHNICAL FIELD

The present invention relates to an antidepressant containing, as an active ingredient, a branched amino acid or a pharmaceutically acceptable salt thereof, or a derivative thereof.

BACKGROUND ART

In recent years, an increasing number of people suffer from depression. When patients suffering so-called masked depression without any psychotic manifestation are included, the total number of such people accounts for a significant proportion, and it is said that one out of every five Japanese will experience depression once in their lives.

The causes of depression still remain uncertain at this time, and are not limited to biological factors and personality factors. For example, the current severe changes in the social environment, the social structure where the weak are abandoned, and the trend for one-dimensional values eliminating heresy are involved in the increase of depression patients.

The therapy of depression includes: first of all, rest; next, drug therapy; and a combination thereof. However, most people are not really allowed to take a rest, and therefore they actually distract themselves with antidepressants.

There are various kinds of antidepressants from those called first generation including imipramine to those called fourth generation including the latest milnacipran. However, these antidepressants can cause side effects such as dry mouth, constipation, urination disorder and anuresis. In addition, there is concern about interaction with other drugs.

Meanwhile, examples of known agents containing a branched amino acid that is an active ingredient of the present invention include an agent for relieving muscular pain and muscle strain and stiffness by oral ingestion of a branched amino acid (see JP-A 2000-26289) and an agent for maintaining instantaneous or sustaining muscular power during exercise by oral ingestion of a branched amino acid (see JP-A 2000-26290). By focusing on the fact that branched amino acids such as leucine, isoleucine and valine have organ-specificity so that they can be utilized mainly in muscles and in tissues such as kidney other than liver, it is found that the branched amino acids are useful in ameliorating muscular pain and muscle stiffness or in maintaining instantaneous or sustaining muscular power during exercise. Also known is an agent for relieving fatigue in the central nervous system containing a branched amino acid (see WO2002/034257) or the like. The document elucidates the mechanism of fatigue in the central nervous system and simultaneously demonstrates that 2-aminobicyclo[2,2,1]heptane-2-carboxylic acid that is a specific inhibitor of L-system transporter in the blood-brain barrier, can suppress the fatigues in the central nervous system, particularly almost completely when used in combination with a branched amino acid such as leucine, isoleucine or valine. In addition, a composition for improving brain cell metabolism (see JP-A 2-172915) and an anti-dementia drug (see JP-A 3-275631), both containing a branched amino acid, are known. However, these documents do not describe that branched amino acids have antidepressant activity.

Known pharmaceutical preparations containing branched amino acids include: a pharmaceutical jelly containing, as active ingredients, only branched amino acids having excellent flavor and excellent feel in swallowing, the jelly being administered in reduced dosage (see JP-A 2003-221330); a pharmaceutical dry syrup containing branched amino acids, a suspending agent and a surfactant, the dry syrup having improved flavor and feel in drinking, and keeping excellent suspensibility when suspended (see JP-A 2003-221329); and a chewable tablet containing, as active ingredients, branched amino acids, the tablet remaining uncolored during storage because of its excellent storage stability (see JP-A 2003-221327). However, none of these documents describes antidepressant activity.

SUMMARY OF INVENTION

Technical Problem

An object of the present invention is to provide an antidepressant.

Solution to Problem

The present inventors made extensive investigation to solve the problem described above, found that a branched amino acid or a pharmacologically acceptable salt thereof, or a derivative thereof can suppress depressive symptoms, and finally completed the present invention.

That is, the present invention relates to:

(1) an antidepressant, which contains, as an active ingredient, at least one compound selected from a branched amino acid, a pharmaceutically acceptable salt thereof and a derivative thereof;

(2) the antidepressant according to the above-mentioned (1), wherein the branched amino acid is at least one compound selected from L-valine, L-leucine and L-isoleucine;

(3) the antidepressant according to the above-mentioned (2), wherein the antidepressant contains at least L-isoleucine;

(4) the antidepressant according to the above-mentioned (3) wherein the content ratio of L-isoleucine, L-leucine and L-valine in terms of molar ratio is 1:(0 to 3):(0 to 2) ;

(5) the antidepressant according to any one of the above-mentioned (1) to (4) , wherein the antidepressant further contains a carbohydrate;

(6) the antidepressant according to the above-mentioned (5), wherein the carbohydrate is glucose; and (7) the antidepressant according to any one of the above-mentioned (1) to (6), which is in the form of an injection or granules.

The present invention also relates to:

(8) a method for preventing or treating depression, which comprises administering a mammal at least one compound selected from a branched amino acid, a pharmaceutically acceptable salt thereof and a derivative thereof;

(9) a use of at least one compound selected from a branched amino acid, a pharmaceutically acceptable salt thereof and a derivative thereof, for producing an antidepressant; and

(10) a use of at least one compound selected from a branched amino acid, a pharmaceutically acceptable salt thereof and a derivative thereof, as an antidepressant.

The present invention also relates to:

(11) a food composition for improving depression, which contains, as an active ingredient, at least one compound selected from a branched amino acid, a pharmaceutically acceptable salt thereof and a derivative thereof.

Advantageous Effects of Invention

According to the present invention, it is possible to improve depression or prevent falling into depression since a branched amino acid, especially isoleucine, has antidepressant activity. The antidepressant of the present invention is almost free of side effects such as dry mouth, constipation, urination disorder and anuresis caused by conventional antidepressants, and basically has no risk of interaction with other drugs. Therefore, the antidepressant of the present invention has high safety and can be continuously administered.

BRIEF DESCRIPTION OF DRAWING

FIG. 1 shows the time rats took to come out of a cylinder in Test Example 1. In the graph, the ordinate shows time.

DESCRIPTION OF EMBODIMENTS

Hereinafter, the antidepressant of the present invention containing, as an active ingredient, at least one compound selected from a branched amino acid, a pharmaceutically acceptable salt of the branched amino acid, and a derivative of the branched amino acid or the pharmaceutically acceptable salt thereof will be described in detail.

The branched amino acids used in the present invention are not particularly limited so long as they meet the standards of the Japanese Pharmacopoeia, and examples of such branched amino acids include any branched amino acid such as L-amino acids, D-amino acids, α-amino acids, β-amino acids, γ-amino acids, natural amino acids, synthetic amino acids and the like, preferably natural L-amino acids or α-amino acids. Particularly preferable examples of the branched amino acids used in the present invention include L-valine, L-leucine and L-isoleucine. The above-mentioned branched amino acids may be prepared by hydrolyzing plant-derived or animal-derived proteins with a protease etc., or by microbial fermentation methods, or may be synthetic amino acids prepared by introducing amino groups into organic acids, etc.

The pharmaceutically acceptable salts of the branched amino acids in the present invention are salts of acids or bases and are not particularly limited, and examples thereof include alkali metal salts such as sodium salts and potassium salts, alkaline earth metal salts such as calcium salts, inorganic acid salts such as hydrochlorides, and organic acid salts such as acetates, and among them hydrochlorides are preferable. Specific examples include L-valine hydrochloride, L-leucine hydrochloride and L-isoleucine hydrochloride.

The derivatives of the branched amino acids or the pharmaceutically acceptable salts thereof used for the antidepressant of the present invention are not particularly limited, and examples include esters and peptides. The esters are not particularly limited as long as they are lower alkyl esters such as methyl ester, ethyl ester, propyl ester and isopropyl ester. The lower alkyl in this case is preferably an alkyl group containing 1 to 6 carbon atoms. Specific examples of the esters preferably include L-valine ethyl ester, L-leucine ethyl ester and L-isoleucine ethyl ester. The peptides are not particularly limited as long as they are oligopeptides such as dipeptides and tripeptides, and specific examples of the peptides preferably include L-isoleucyl-L-leucine, L-alanyl-L-leucine, L-leucyl-L-alanine and glycyl-L-leucine. Accordingly, amino acids other than the branched amino acid that constitute the oligopeptides may be any amino acid including L-amino acids, D-amino acids, α-amino acids, β-amino acids, γ-amino acids, natural amino acids, synthetic amino acids and the like.

In the antidepressant of the present invention, these branched amino acids or pharmaceutically acceptable salts thereof or derivatives thereof can be used alone or as a mixture of two or more thereof, but at least L-isoleucine or a salt thereof or a derivative thereof, in particular at least L-isoleucine is preferably contained.

In the present invention, when two or more of these branched amino acids or pharmaceutically acceptable salts thereof or derivatives thereof are used, their mixing ratio is not particularly limited. Specifically when the branched amino acid or pharmaceutically acceptable salts thereof or derivatives thereof, for example, L-isoleucine, L-leucine and/or L-valine are used, these compounds may be used alone or as a mixture of two or more thereof, and the mixing ratio of the compounds, in terms of molar ratio, is preferably L-isoleucine:L-leucine:L-valine=about 1:(0 to 3):(0 to 2), and more preferably about 1:(0 to 2.5):(0 to 1.5). When salts of, for example, L-isoleucine, L-leucine and/or L-valine, or derivatives thereof are used, they are used preferably in the above molar ratio in terms of L-isoleucine, L-leucine and L-valine, respectively.

Preferably, the antidepressant of the present invention further contains a carbohydrate. The carbohydrate includes, but is not limited to, monosaccharides such as ribose, deoxyribose, glucose, fructose and galactose; disaccharides such as maltose, trehalose, sucrose and lactose; and polysaccharides such as amylose, amylopectin and glycogen. Among the carbohydrates, monosaccharides are more preferable, and glucose is particularly preferable because it can serve as an immediately-usable energy source in a living organism.

In this case, the content ratio of carbohydrates is not particularly limited, but is preferably for example about 0.1 to 50 moles in terms of glucose per 1 mole of a branched amino acid. The content ratio of carbohydrates is preferably about 0.1 to 20 moles, and more preferably about 0.2 to 10 moles in terms of glucose per 1 mole of a branched amino acid.

The antidepressant of the present invention can be provided in the form of medicine containing a pharmaceutically acceptable additive or in the form of food containing an additive approved under the food sanitation law.

The antidepressant of the present invention, when formed into a medicine, can be used for example as a solid preparation for oral administration, a liquid medicine for oral administration, or an injection for parenteral administration (subcutaneous, intravenous, intramuscular or intraperitoneal injection etc.). The solid preparation for oral administration includes, for example, tablets, pills, capsules, powder and granules.

The additives that can be used in the solid preparation for oral administration include, for example, an excipient, a binder, a disintegrating agent, a lubricant, a stabilizer and a wetting agent. The excipient includes, but is not limited to, sucrose, lactose, glucose, starch and mannitol. The binder includes, but is not limited to, gum arabic, carmellose, gelatin, crystalline cellulose, hydroxypropyl cellulose, methyl cellulose and povidone. The disintegrating agent includes, but is not limited to, carmellose, starch, crystalline cellulose and low-substituted hydroxypropyl cellulose. The lubricant includes, but is not limited to, talc, magnesium stearate, calcium stearate and silica. The stabilizer and the wetting agent include, but are not limited to, citric anhydride, sodium laurate and glycerol. These additives can be used alone or in combination of two or more kinds. The solid preparation for oral administration can be prepared for example by mixing a branched amino acid, a salt thereof or a derivative thereof with an additive etc., and then forming the mixture into a pharmaceutical preparation according to general methods described in, for example, general rules in the Japanese Pharmacopoeia, $14^{th}$ revised edition. Specifically, the granules can be preferably prepared for example by adding the above-described excipient, binder, disintegrating agent, etc. to a branched amino acid, a salt thereof or a derivative thereof, kneading the mixture uniformly, and then forming the mixture into granules through compression granulation, tumbling granulation, spray drying granulation, extrusion granulation, milling granulation, fluidization granulation, agitation granulation or the like. The tablets can be produced for example by adding the above-described excipient, binder, disintegrating agent, etc. to a branched amino acid, a salt thereof or a derivative thereof, kneading the mixture uniformly, and then directly performing compression molding; or by preparing granules from a branched amino acid, a salt thereof or a derivative thereof and the excipient, binder, disintegrating agent, etc., and then forming the granules, as they are or after being uniformly mixed with the above-described additive added thereto, into tablets by compression molding. The granules or tablets may be coated if necessary with a suitable coating (gelatin, sucrose, gum arabic, carnauba wax etc.) or an enteric coating (for example, cellulose acetate phthalate, a methacrylic acid copolymer, hydroxypropyl cellulose phthalate, carboxymethylethyl cellulose, etc.). The capsules can be produced for example by adding the above-described excipient, binder, disintegrating agent, etc. to a branched amino acid, a salt thereof or a derivative thereof, kneading the mixture uniformly, optionally forming the mixture into granules, optionally coating the granules with a coating agent, and charging the mixture, granules, or coated granules into capsules.

The content ratio of a branched amino acid, a salt thereof or a derivative thereof in the solid preparation for oral administration is not particularly limited, but preferably the total amount of branched amino acids is about 1 to 90% by mass relative to the whole solid preparation.

The liquid medicine for oral administration includes, for example, a drench, a suspension, an emulsion, a syrup and an elixir. Additives usable in such a liquid medicine include, for example, a solvent such as purified water, ethanol, a mixture thereof, etc. The liquid medicine for oral administration may further contain, for example, a suspending agent (for example, gum arabic, agar, carmellose, hydroxypropyl cellulose, etc.), an emulsifying agent (for example, polysorbate 80, gum arabic, etc.) a flavoring substance (for example, simple syrup, honey, sucrose, tartaric acid etc), an aromatic substance (for example, methyl salicylate, fennel oil, orange oil, menthol etc.), a preservative (for example, benzoic acid, sodium benzoate, etc.) and a buffering agent (for example, citric acid, hydrogen carbonate, etc.). These additives can be used alone or in combination of two or more kinds.

Additives that can be used in an injection for parenteral administration include, for example, a solvent, a stabilizer, a solubilizing agent, a suspending agent, a surfactant, an emulsifying agent, a soothing agent, a buffering agent and a preservative. The solvent includes, but is not limited to, distilled water for injection, physiological saline, vegetable oil such as sesame oil, ethyl alcohol, isopropyl alcohol, propylene glycol, 1,3-butylene glycol and polyethylene glycol. The stabilizer and the solubilizing agent include, but are not limited to, glutamic acid, aspartic acid and polysorbate 80. The suspending agent includes, but is not limited to, cellulose derivatives such as carboxymethyl cellulose sodium and methyl cellulose, and natural gum such as tragacanth and gum arabic. The surfactant includes, but is not limited to, sorbitan fatty acid ester, polyoxyethylene sorbitan fatty acid ester, polyoxyethylene fatty acid ester, polyoxyethylene ether of hydrogenated castor oil, and lecithin. The emulsifying agent includes, but is not limited to, polyoxyl stearate, lauromacrogol, polysorbate 80 and gum arabic. The soothing agent includes, but is not limited to, ethyl aminobenzoate, inositol, meprilcaine hydrochloride, lidocaine hydrochloride, chlorobutanol, propylene glycol and benzyl alcohol. The buffering agent includes, but is not limited to, citric acid or a salt thereof glucose, phosphoric acid or a salt thereof, and acetic acid or a salt thereof. The preservative includes, but is not limited to, p-hydroxybenzoate ester, benzalkonium chloride, and sorbitan acid salt. These additives can be used alone or in combination of two or more kinds.

The injection can be produced in a usual manner, for example by suitably dissolving a branched amino acid, a salt thereof or a derivative thereof and an additive etc., by aseptic manipulation. The produced injection is charged into an ampoule, a vial container, a glass or polyethylene infusion container (including a bag) or the like and then sterilized. The polyethylene infusion container (including a bag) may be packaged for example in a gas-barrier packaging material together with a deoxygenating agent etc. The injection may be produced in a form of a sterile solid preparation, for example a lyophilized product, which can be used by being dissolved in sterilized or sterile distilled water for injection or in another solvent just before use.

The content ratio of a branched amino acid, a salt thereof or a derivative thereof is not particularly limited, but in the case of an infusion preparation, the total amount in terms of free branched amino acids is preferably about 0.1 to 10 w/v %, more preferably about 0.1 to 5 w/v %, more preferably about 0.5 to 3 w/v %, relative to the whole injection.

The antidepressant of the present invention may further contain nutrients such as vitamins (for example, vitamin A, vitamins B1, B2, B6, B12, vitamin C, vitamin D, vitamin E, niacin, pantothenic acid, folic acid, biotin, vitamin F, vitamin P, vitamin Q, vitamin U, choline, inositol, p-aminobenzoic acid, etc.) and amino acids other than branched amino acids (for example lysine, phenylalanine, methionine, threonine, valine, histidine, tryptophan, alanine, proline, arginine, glutamic acid, serine etc.).

The dosage of the medicine containing the antidepressant of the present invention is not particularly limited and may be determined depending on the formulation, administration route, the age and weight of the patient, the severity of the disease, etc. General daily dosage per 1 kg of adult body weight may be within the range of about 1 to 1000 mg, preferably about 1 to 500 mg, more preferably about 10 to 500 mg, further more preferably about 50 to 300 mg in terms of free branched amino acids, and may be suitably increased or decreased as desired. The medicine may also be administered in several doses a day.

When the antidepressant of the present invention is formed into a food, at least one of a branched amino acid, a salt thereof and a derivative thereof, preferably L-isoleucine, is mixed with an additive approved under the food sanitation law or with other various components used for food to form a food or drink product. The form of the food to be produced is not particularly limited, and the food may be in every possible form such as tablets, capsules, powder, granules, a liquid medicine for oral administration, a solid food, a semi-liquid food in the form of cream or jam, a gelatinous food and a drink. Specific examples of the food include, for example, drinks such as soft drinks, juice or lactic acid bacteria beverage, jelly, candies, biscuits and cookies. The method for producing the food is not particularly limited, and any means known in the art can be used.

The above-mentioned food preferably contains, in addition to a branched amino acid, a salt thereof or a derivative thereof, a carbohydrate, dietary fiber, etc., and more preferably contains a carbohydrate. Examples of the carbohydrate include the above-mentioned saccharide, preferably monosaccharide, in particular glucose. The content ratio of carbohydrates in proportion to a branched amino acid is the same as in the case of the above-mentioned antidepressant. The dietary fiber is particularly preferably indigestible dextrin.

The tablets, capsules, powder, granules or liquid preparation for oral administration can be produced in the same manner as in the production of the above-described medicine except that an additive approved under the food sanitation law (for example, hydroxypropylmethyl cellulose, crystalline cellulose, tartaric acid, mannitol, saccharine sodium, stevia, dimethylpolysiloxane, p-hydroxybenzoate ester, etc.) is used in place of the additive used in the tablets, capsules, powder, granules or liquid medicine for oral administration as the medicine described above.

The drink to be produced may contain additives, for example, flavoring substances such as a flavor, a colorant, natural juice, fruit pulp, cheese and chocolate, and a synthetic sweetener as needed. The additives may be used alone or in combination of two or more kinds.

The semi-liquid food in the form of cream or jam or the gelatinous food such as jelly, to be produced, may preferably contain one or more gelling agents selected from agar, gelatin, carrageenan, gellan gum, xanthan gum, locust bean gum, pectin, sodium alginate, potassium alginate and other ordinarily used polysaccharide thickeners, in addition to the above-mentioned components of a drink. The blending amount of the gelling agent is about 2 parts by mass or less, preferably about 0.5 to 2 parts by mass per 100 parts by mass of jelly.

The content ratio of a branched amino acid, a salt thereof or a derivative thereof in such a food is not particularly limited, but preferably the total amount in terms of free branched amino acids is preferably about 1 to 60% by mass. The total amount in terms of free branched amino acids in the food is preferably about 10 to 60% by mass, more preferably about 15 to 60% by mass.

The food produced in this manner can be used as a functional food for improving depression. A food composition for improving depression, containing at least one compound selected from such a branched amino acid, a pharmaceutically acceptable salt thereof and a derivative thereof, is also included in the present invention. An indication of its effect of improving depression is preferably provided on the package etc. of such a food product.

The food is ingested preferably in a daily amount of about 0.1 to 20 g in terms of free branched amino acids per adult (about 60 kg). The daily food intake in terms of free branched amino acids per adult (about 60 kg) is more preferably about 1 to 20 g, further preferably about 3 to 20 g, and particularly preferably about 5 to 20 g.

By administering a mammal an effective dose of at least one compound selected from a branched amino acid, a pharmaceutically acceptable salt thereof and a derivative thereof, depression can be prevented, improved or treated. The mammal as the subject of administration is typically a human, and preferable examples include a human with depression, and a human in a state with risk of moving into depression (a human with masked depression, a human with extreme stress, etc.). Prevention includes, for example, suppression of the progress into depression from a state with risk of moving into depression, suppression of the development of depression from a healthy condition.

A method for preventing or treating depression comprising administering a mammal at least one compound selected from the above-mentioned branched amino acid, a pharmaceutically acceptable salt thereof and a derivative thereof, is also included in the present invention. In the method of the present invention for preventing or treating depression, preferred is that an antidepressant containing, as an active ingredient, at least one compound selected from the above-mentioned branched amino acid, a pharmaceutically acceptable salt thereof and a derivative thereof is produced and administered. It is also preferred that a food composition containing at least one compound selected from the above-mentioned branched amino acid, a pharmaceutically acceptable salt thereof and a derivative thereof, is produced and ingested by a mammal.

A use of at least one compound selected from a branched amino acid, a pharmaceutically acceptable salt thereof and a derivative thereof, for producing an antidepressant; and a use of at least one compound selected from a branched amino acid, a pharmaceutically acceptable salt thereof and a derivative thereof, as an antidepressant are also included in the present invention. A preferred embodiment of an antidepressant produced with the use of at least one compound selected from a branched amino acid, a pharmaceutically acceptable salt thereof and a derivative thereof, is the same as that of the above-mentioned antidepressant.

EXAMPLES

Hereinafter, the present invention is described in more detail by reference to Production Examples and Test Example, but the present invention is not limited to these examples.

Production Example 1

300 g of L-isoleucine was dissolved in distilled water for injection. The solution was adjusted to pH 6.50 with sodium hydroxide and then adjusted to a total volume of 10 L with distilled water for injection. The resulting solution was filtered through a membrane filter, introduced into polyethylene infusion bags so that each bag would contain 500 mL, sealed, and sterilized at 105° C. for 40 minutes by autoclaving. The bag, together with an oxygen absorber (trade name: Ageless, manufactured by Mitsubishi Gas Chemical Co., Inc.), was packaged in a gas-barrier packaging material made of a polyvinyl alcohol multilayer to give an injection.

Production Example 2

150 g of L-isoleucine and 150 g of L-valine were dissolved in distilled water for injection. The solution was adjusted to pH 6.50 with sodium hydroxide and then adjusted to a total volume of 10 L with distilled water for injection. The resulting solution was filtered through a membrane filter, introduced into polyethylene infusion bags so that each bag would contain 500 mL, sealed, and sterilized at 105° C. for 40 minutes by autoclaving. The bag, together with an oxygen absorber (trade name: Ageless, manufactured by Mitsubishi Gas Chemical Co., Inc.), was packaged in a gas-barrier packaging material made of a polyvinyl alcohol multilayer film, to give an injection.

Production Example 3

300 g of L-isoleucine was dissolved in distilled water for injection. The solution was adjusted to pH 6.50 with sodium hydroxide, adjusted to a total volume of 10 L with distilled water for injection, and filtered through a membrane filter.

Separately, 1000 g of glucose was dissolved in distilled water for injection. The solution was adjusted to a total volume of 10 L with distilled water for injection, and filtered through a membrane filter.

500 ml each of these solutions were separately introduced into different chambers of a polyethylene two-chamber infusion bag, sealed, and sterilized at 105° C. for 40 minutes by autoclaving. The bag, together with an oxygen absorber (trade name: Ageless, manufactured by Mitsubishi Gas Chemical Co., Inc.), was packaged in a gas-barrier packaging material made of a polyvinyl alcohol multilayer film, to give an injection.

When used, by pressing one chamber or two chambers of the bag, the two chambers are linked to each other to prepare a mixture to be used as an injection.

Production Example 4

1000 g of L-alanyl-L-leucine, 300 g of L-isoleucine and 240 g of L-valine were dissolved in distilled water for injection. The solution was adjusted to pH 6.50 with sodium hydroxide and then adjusted to a total volume of 10 L with distilled water for injection. The resulting solution was filtered through a membrane filter, introduced into polyethylene infusion bags so that each bag would contain 100 mL, sealed and sterilized at 105° C. for 40 minutes by autoclaving. The bag, together with an oxygen absorber (trade name: Ageless, manufactured by Mitsubishi Gas Chemical Co. Inc.), was packaged in a gas-barrier packaging material made of a polyvinyl alcohol multilayer film, to give an injection.

Production Example 5

120 g of hydroxypropylmethyl cellulose and 10 g of crystalline cellulose carmellose sodium were added to, and dispersed in, 10 L of purified water. To this dispersion, 100 g of tartaric acid, 1000 g of mannitol, 10 g of saccharine sodium, 5 g of stevia, 40 g of dimethylpolysiloxane, 2 g of propyl p-hydroxybenzoate and 5 g of methyl p-hydroxybenzoate, were added and dissolved. Subsequently, 950 g of L-isoleucine, 1900 g of L-leucine and 1150 g of L-valine were added thereto and suspended with a homogenizer. This suspension was adjusted to pH 6.5 with sodium hydroxide and further suspended with a homogenizer to prepare a uniform suspension.

Separately, 40 g of agar powder was added to 2 L of purified water and dissolved by heating to about 80° C. To this, 6000 g of the above suspension and 40 g of a pineapple flavor were added, and mixed. The resulting mixture was introduced into containers so that each container would contain 100 g, sealed, and chilled to prepare a jelly.

Production Example 6

500 g of L-isoleucine, 1000 g of L-leucine, 600 g of valine, 100 g of citric anhydride and 50 g of hydroxypropyl cellulose were mixed uniformly, and then 300 g of distilled water was added to the mixture, which was then granulated.

The granulated product was dried at 60° C. for 2 hours and passed through a 24-mesh sieve to give granules. The resulting granules were introduced into aluminum laminate stick bags so that each bag contains 4.5 g, and sealed, to give a final product.

Test Example 1

Antidepressant Activity of Orally Administered Branched Amino Acid

SD rats (10-week-old) were divided into two groups (10 rats in each group). One group (control group) was kept for 6 days with free access to food (standard AIN-76 diet manufactured by Nosan Corporation) and water. The other group (present invention group) was kept for 6 days with free access to food (standard AIN-76 diet containing 1% by mass of L-isoleucine) and water. Using these subject animals, depression-improving activity in rats under stress was tested according to the defensive withdrawal test method by Gutman, D. A. et al. (The Journal of Pharmacology and Experimental Therapeutics, 304 (2), 874 (2003)).

That is, a rat (one from each group) was dropped, tail first, into an upright black cylinder 10 cm in diameter and 20 cm in length, and immediately covered with a lid. After 10 seconds, the cylinder was placed in an open field (100 cm long, 100 cm wide, and 45 cm high) made up of white acrylic boards, facing one corner, at a position 20 cm from the corner. The lid was taken off immediately, and behavior of the rat was observed for 5 minutes to measure the time the rat took to come out of the cylinder.

The test was carried out under an illuminance of 200 1× in a soundproof room, and behavior of the rat was videotaped from above and observed using a monitor outside the soundproof room.

Statistical processing was performed by two-sided Student's t-test.

The results are shown in FIG. 1. Compared to the control group, the present invention group took significantly shorter time to come out of the cylinder, which proved the antidepressant effect of L-isoleucine.

The same tests were done using L-leucine or L-valine, and the same antidepressant effect as that of L-isoleucine was confirmed.

Industrial Applicability

The antidepressant of the present invention can improve depression or prevent falling into depression and can be continuously administered because of its high safety. Therefore, the antidepressant can be used in medicine or food.

The invention claimed is:

1. A method for treating depression in a mammal in need thereof, consisting of administering to said mammal a formulation comprising active ingredients consisting of:

(a) L isoleucine, L-leucine and L-valine wherein the molar ratio of L-isoleucine:L-leucine:L-valine is in the range from 1:(1.22-2.5):(0.9-1.5);

wherein at least one amino acid selected from L-isoleucine, L-leucine and L-valine may be its pharmaceutically acceptable salt; and (b) glucose, wherein the glucose is present in a molar ratio of about 0.1 to 50 moles per 1 mole of one of the amino acids set forth in (a).

2. The method according to claim 1, wherein the glucose is present in a molar ratio of about 0.1 to 20 moles per 1 mole of one of the amino acids selected from the group consisting of L-isoleucine, L-leucine and L-valine.

3. The method according to claim 2, wherein the glucose is present in a molar ratio of about 0.1 to 10 moles per 1 mole of one of the amino acids selected from the group consisting of L-isoleucine, L-leucine and L-valine.

4. The method according to claim 1, wherein said formulation is administered to said mammal in a form selected from the group consisting of an injection and granules.

5. The method according to claim 1, wherein said formulation is administered to said mammal in the form of a food composition.

6. The method according to claim 5, wherein said food composition comprises about 1% to 60% of L-isoleucine, L-leucine and L-valine by mass.

7. The method according to claim 6, wherein said food composition comprises about 10% to 60% of L-isoleucine, L-leucine and L-valine by mass.

8. The method according to claim 7, wherein said food composition comprises about 15% to 60% of L-isoleucine, L-leucine and L-valine by mass.

9. A method of using branched amino acids and glucose, as an antidepressant consisting of:

identifying a patient as being in need of therapy for depression, and delivering to said patient a pharmaceutically effective amount of a formulation consisting of:

(a) L isoleucine, L-leucine and L-valine wherein the molar ratio of L-isoleucine:L-leucine:L-valine is in the range from 1:(1.22-2.5):(0.9-1.5);

wherein at least one amino acid selected from L-isoleucine, L-leucine and L-valine may be its pharmaceutically acceptable salt; and (b) glucose, wherein the glucose is present in a molar ratio of about 0.1 to 50 moles per 1 mole of one of the amino acids set forth in (a).

10. The method according to claim 9, wherein the glucose is present in a molar ratio of about 0.1 to 20 moles per 1 mole of one of the amino acids selected from the group consisting of L-isoleucine, L-leucine and L-valine.

11. The method according to claim 10, wherein the glucose is present in a molar ratio of about 0.1 to 10 moles per 1 mole of one of the amino acids selected from the group consisting of L-isoleucine, L-leucine and L-valine.

12. The method according to claim 9, wherein said formulation is administered to said patient in a form selected from the group consisting of an injection and granules.

13. The method according to claim 9, wherein said formulation is administered to said patient in the form of a food composition.

14. The method according to claim 13, wherein said food composition comprises about 1% to 60% of L-isoleucine, L-leucine and L-valine by mass.

15. The method according to claim 14, wherein said food composition comprises about 10% to 60% of L-isoleucine, L-leucine and L-valine by mass.

16. The method according to claim 15, wherein said food composition comprises about 15% to 60% of L-isoleucine, L-leucine and L-valine by mass.

* * * * *